United States Patent [19]

Hughes, Jr. et al.

[11] 4,225,385
[45] Sep. 30, 1980

[54] SHIVE RATIO ANALYZER

[75] Inventors: Horatio Hughes, Jr., Charleston; Robert A. Schilling, Charleston Heights, both of S.C.

[73] Assignee: Westvaco Corporation, New York, N.Y.

[21] Appl. No.: 3,161

[22] Filed: Jan. 15, 1979

Related U.S. Application Data

[63] Continuation of Ser. No. 812,056, Jul. 1, 1977, abandoned.

[51] Int. Cl.$^2$ .................... G01N 15/02; G01N 21/28
[52] U.S. Cl. .................... 162/263; 162/DIG. 10; 73/422 R; 235/92 PC; 250/222 PC
[58] Field of Search ......... 162/49, 198, 263, DIG. 10, 162/238, 262, 50; 356/102, 208, 335, 442; 324/71 CP; 250/222 PC; 73/422 R, 63, 53; 364/471, 555; 235/92 PC

[56] References Cited

U.S. PATENT DOCUMENTS

| | | | |
|---|---|---|---|
| 3,461,030 | 8/1969 | Keyes | 162/DIG. 10 |
| 3,626,166 | 4/1970 | Berg | 324/71 CP |
| 3,714,444 | 1/1973 | Carr et al. | 250/222 PC |
| 3,724,957 | 4/1973 | Tamate et al. | 162/198 X |
| 3,855,455 | 12/1974 | Allinger et al. | 356/102 |
| 3,858,449 | 1/1975 | Singer | 73/422 R |
| 3,879,129 | 4/1975 | Inoue | 356/208 |
| 4,018,089 | 4/1977 | Dzula et al. | 73/422 R |
| 4,021,117 | 5/1977 | Göhde et al. | 356/102 X |
| 4,037,966 | 7/1977 | Hill | 356/102 X |
| 4,066,492 | 1/1978 | Hill | 162/49 |

OTHER PUBLICATIONS

Johnson et al.; "International Mechanical Pulping Conference 1973;" Stockholm, Sweden, (6-1973).
Hill et al.; "Evaluations of Screens by Optical Measurements," *Tappi*; vol. 58, No. 10, pp. 120-124, (10-1975).

*Primary Examiner*—S. Leon Bashore
*Assistant Examiner*—Steve Alvo
*Attorney, Agent, or Firm*—W. Allen Marcontell; Richard L. Schmalz

[57] ABSTRACT

Relative shive incidence in a production flow line of paper pulp is continuously sampled and measured by means of a continuous flow, fiber induction device located within the production line to extract a diluted sample of fiber flow therein. The diluted sample is directed through a windowed conduit section for photodetection of particles therein. Particle caused pulses are discriminated by amplitude relative to a reference scale to distinguish shive particles from acceptable fiber particles. Two pulse trains are developed simultaneously: one pulse train for shive pulses and the other pulse train for particle flow including shives. Both pulse trains are rate determined by counting the number of pulses in a fixed interim of time identical to both. The two pulse rates are then combined to develop a dimensionless ratio of shive incidence or percentage within the total fiber stream.

10 Claims, 7 Drawing Figures

SHIVE RATIO ANALYZER

This is a continuation, of application Ser. No. 812,056, filed July 1, 1977 now abandoned.

BACKGROUND OF THE INVENTION

1. Field of the Invention

The present invention relates to the art of qualitatively measuring the properties of wood pulp in a dilute stock slurry. More specifically, the present invention relates to a method and apparatus for photometrically identifying the percentage of shives in a stock flow stream.

2. Description of the Prior Art

As a broad generalization, the process of pulping wood for papermaking comprises a series of chemical and mechanical steps to disintegrate the natural state of wood into individual or small bundles of cellulose fiber. However, since wood is not a homogenous material, the standardized or uniform process of an industralized pulp flow stream does not have the same result on all elements of a tree.

One particular notable natural wood anomaly is the occurrence of fiber bundles bound together by transverse ray cells. A singular, consolidated bundle grouping is known to the papermaker as a "shive." Such transversely bound bundles are extremely tenacious in their resistance to defiberizing processes.

Although wood pulp is normally screened one or more times along the process stream, it is impossible to segregate all shives having 4–8 length and 100 to 140 $\mu$m width from acceptable fiber bundles of less than half the shive size. Nevertheless, it is important to the papermaker that the presence of shives be maintained below a certain percentage quantity in the stock due to their consequential deleterious effect on a paper web.

The generally practiced industry technique for monitoring the relative presence of shives in a pulp stream is to periodically count, manually, the individual shive incidence in a standard area, randomly selected, sample of paper made from the pulp. This practice, of course, is extremely time consuming and occasions a large delay interim between the time that pulp lands upon the papermachine and knowledgeable recognition of the relative shive incidence. Consequently, it is not unusual that machine operators will be plagued with web breaks unacceptable paper quality due to excess shives long before the cause of the trouble is known.

Recently, work has begun on the development of more timely techniques for shive monitoring. One published report of such work is found in the October, 1975 journal of the Technical Association Of The Pulp and Paper Industry (TAPPI, Volume 58, No. 10, page 120. This report describes an optical detector which passes two perpendicularly disposed light beams in a common plane transversely through a windowed conduit carrying a pulp sample stream. Respective photodetector responses to the shading effect of fibers crossing the beam paths are measured to yield a length, width and thickness determination for each fiber. By means of internally programmed limits, the event of a passing shive may be immediately identified and counted. The frequency of such shive counts is compared to the consistency and flow rate of the sample which must be carefully controlled.

Although the aforedescribed optical shive counter manufactured by Tellusond of Stockholm, Sweden, is extremely accurate, it is still a laboratory device which requires the isolation of a pulp sample from the production flow stream for accurate consistency and flow rate control.

Stock consistencies in a production flow stream are maintained in the range of 1 to 4% based on dry fiber weight. However, the Tellusond shive counter requires a batch quantity stock sample accurately measured to 0.01 g/l and a 10 minute processing period for each batch. These circumstances dictate an instrument preparation procedure which includes withdrawal of an adequate stock quantity of substantially unknown consistency from the production line, analyzing the sample for total fiber content and accurately mixing a sufficient stock quantity to an accurately known consistency. This procedure may be mechanized for an automatic sampling and measuring cycle but the necessary support apparatus is elaborate and subject to considerable maintenance.

U.S. Pat. No. 3,461,030 to M. A. Keyes describes a different type of wood pulp slurry measuring device which relies upon the dielectric quality of cellulose to impose a voltage variation between two electrodes as fibers suspended in a known electrolyte are passed therebetween. Similar to the Tellusond optical device, the Keyes instrument integrates a cross-sectional area measurement of an individual fiber with a transit time measurement to derive a volumetric conclusion. Consistency of the slurry is obtained by combining the fiber volume conclusion with a simultaneous slurry volume measurement. Although the Keyes instrument is disclosed in the context of a consistency measuring instrument, it is conceivable that it may be adapted to shive measurement simply because it obtains a quantitative measure of individual fiber or particle volume. Nevertheless, the inventor did not disclose a recognition of this capacity or how such an adaptation may be devised.

In light of such aforedescribed prior art, there heretofore remained a need for an instrument that will continuously measure the relative presence of shives in a mill production stock flow stream. The specification of this need by the pulp and papermaking industry is further complicated by the absence of a satisfactory pulp sampling technique that is simple, continuous and relatively maintenance free.

Cellulose fibers have an unusually high affinity for adhesion to each other and to foreign surfaces. Any surface exposed to a pulp stream is quickly coated with a layered growth of fiber. This growth continues until other forces such as gravity or fluid shear exceed the adhesion strength of the fiber bond thereby causing a breaking off of an accumulated quantity. Consequently, maintenance of a continuous flow stream of pulp is a scalar and velocity design problem. Relatively small pipelines will be quickly plugged by fiber accumulations if not self-cleaned by an appropriately high flow velocity. For these reasons it is difficult to continuously extract from a large production line a small but representative sample of pulp for testing purposes. Accordingly, it is also an objective of the present invention to teach a method and apparatus for continuously extracting a low quantity pulp sample that is representative of the primary flow stream but will not plug.

BRIEF SUMMARY OF THE INVENTION

The present invention accomplishes these and other objectives by means of a continuous pulp sample extraction device which directs a fiber-free water stream across an open gap within a large production flow stream of pulp into a sample extraction conduit. Pressure on the fiber free water stream is significantly higher than the production line pressure to maintain a relatively low energy loss across the open gap. Principles of fluid flow induction draw pulp fiber from the production stream in the proximity of the gap to be carried along the extraction conduit. Although consistency dilution occurs, the sample extraction flow stream is sustained at a substantially constant flow rate, therefore, the quantity of pulp extracted at any given moment may be directly related to the momentary production stream consistency.

For purposes of shive density monitoring the sample extraction flow stream is adjusted to provide an approximate 0.05% pulp consistency although this value is not particularly critical. A consistency of 0.1% or less is suitable.

The dilute sample is then conducted past a photometric window between a light source and a single photodetector having an approximate ½ inch (1.25 cm) flow channel gap therebetween.

Voltage measuring devices signify both the event of a passing fiber or shive and the relative size thereof due to the particle shadow on the detector. The magnitude of voltage response to such passing shadows is directly related to the size of the shadow and hence, the size of the particle. Since shives are significantly larger than acceptable fiber bundles, the detector voltage responses may be segregated accordingly by appropriate signal discriminating devices.

Simultaneously, signals proportional to the absolute or total particle flow rate are ratioed with the total shive flow rate to yield a signal that is directly proportional to the shive density in the sample stream.

Accurate knowledge of sample consistency is irrelevant since the invention relates a first counted number of particles to a second counted number of shives, the first number being inclusive of the second number. Consequently, the absolute quantity of these numbers in the sense of consistency or dry pulp quantity per unit slurry volume is unnecessary to conclude the desired objective of shive density.

Accordingly, a continuous indication of shive density may be reported in such form as to automatically actuate appropriate alarms when the density exceeds acceptable limits. Moreover, the point in the production flow stream at which the sample is extracted may be selectively chosen sufficiently far upstream of the papermachine headbox so as to provide adequate time for evasive or corrective action before a high shive density increment of pulp enters the headbox.

BRIEF DESCRIPTION OF THE DRAWING

Relative to the drawing wherein like reference characters designate like or similar elements throughout the several figures.

DESCRIPTION OF THE PREFERRED EMBODIMENT

Figure 1:
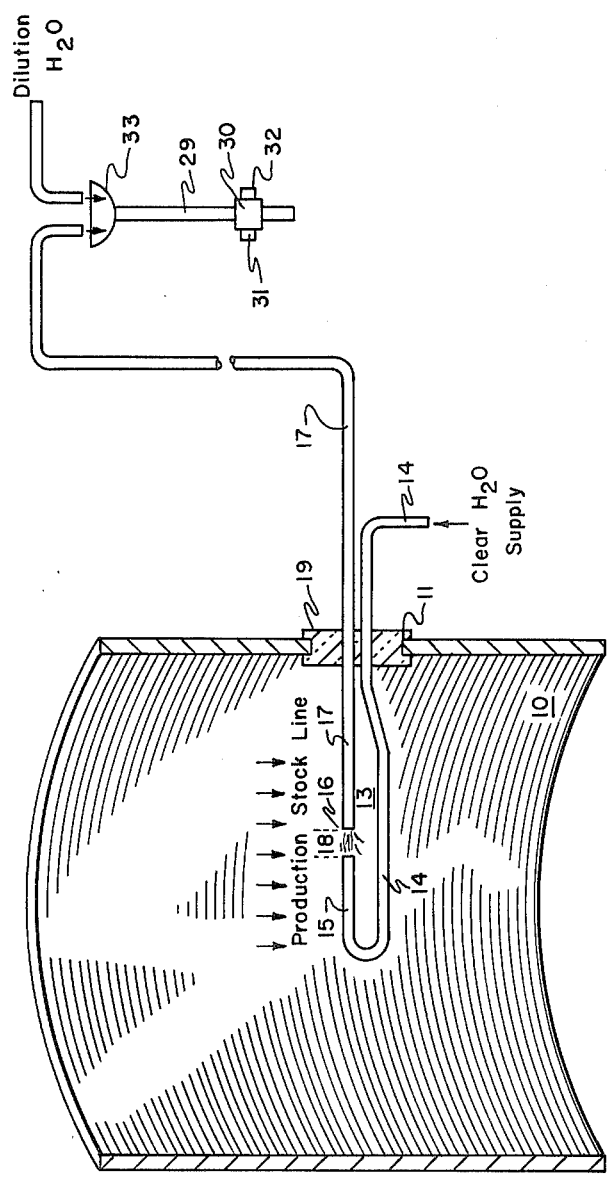
FIG. 1 is a piping schematic for the present pulp sampling system.

The mechanical schematic of FIG. 1 illustrates the sample extraction system of the invention which may be inserted through a single aperture 11 in a production stock line pipe or vessel wall 10. The wand 13 of the extractor comprises a small conduit 14 for the delivery of fiber-free water at a relatively constant flow rate to a discharge nozzle 15 which is axially aligned with a square cut opening 16 of extraction conduit 17.

A gap 18 is provided between the tip of nozzle 15 and opening 16. This gap 18 is positioned centrally within the stock line 10 to be swept by a representative flow of the stock therein. Regarding cross-sectional placement of the gap 18 within the production line, the usual instrumentation caveats apply such as avoidance of flow stagnation regions in pipe bends and near the side walls.

Grommet 19 provides a fluid pressure seal of the aperture 18 around the conduits 14 and 17.

There is little criticality in the design parameters of the sample extraction system except that the clear water supply pressure in conduit 15 should be substantially greater than that of the stock line pressure. The system bears resemblance to a conventional jet pump or aspirator except for the gap 18. In the case of jet pumps and aspirators, release of the energy carrying jet stream occurs within the boundary confines of a larger volume induction chamber to provide a localized low pressure zone having communication with the induced fluid. None of the energy carrying induction fluid is lost from the flow system and no intermingling of the induced and induction fluids occurs outside of the induction chamber boundary. In the case of the present invention, intermingling of the induced and induction fluids occurs in the relatively infinite volume of the induced fluid vessel. Moreover, induction fluid may be, and in all probability is, lost from the total flow stream. Although energy efficiency of the present invention is less than that of jet pumps and aspirators, this circumstance is, in absolutes, insignificant or irrelevant to the objective of extracting a low volume sample flow from the 1% to 4% consistency main stream 10 free of pipe plugging concerns.

In a representative actual use of the invention, a ¼ conduit 15 carring a 1 gpm flow rate at 50 psi disscharged a jet stream across a ⅜ inch gap 18 through and transversely of a 4.5% consistency, 0.5 psi pulp flow stream into the bare open end of a ¼ inch conduit to lift an approximately 0.5 to 1.0% consistency pulp sample through a 10 foot head.

Of course, system designs may be optimized from the perspective of minimum energy loss across the gap 18 and maximum total head and velocity within the extraction tube 17. However, from the specific example described, simple experimentation will usually provide an operative system suitable for the following objectives.

As a further note to the sample extraction system, the described circumstance of jet stream discharge nozzle 15 having the same dimensional size as the sample line 17 capture opening 16 should not be considered as a limiting specification since relatively larger area capture openings 16 are known to operate well and in some circumstances, with greater efficiency. Similarly, divergent capture openings 16 have been successfully utilized. Such divergent opening arrangements are physically configured to a convergent-divergent venturi with the throat region removed to accommodate the mixing gap 18.

The extracted sample flow in conduit 17, if within the broad consistency range of less than 0.1% tolerated by the shive meter, may be delivered directly through a transparent window pipe section 30 between a light source 31 and a photodetector 32. Should consistency of the extracted stock sample prove greater than the suggested maximum, additional dilution water may be added at a mixing point 33.

Figure 2:
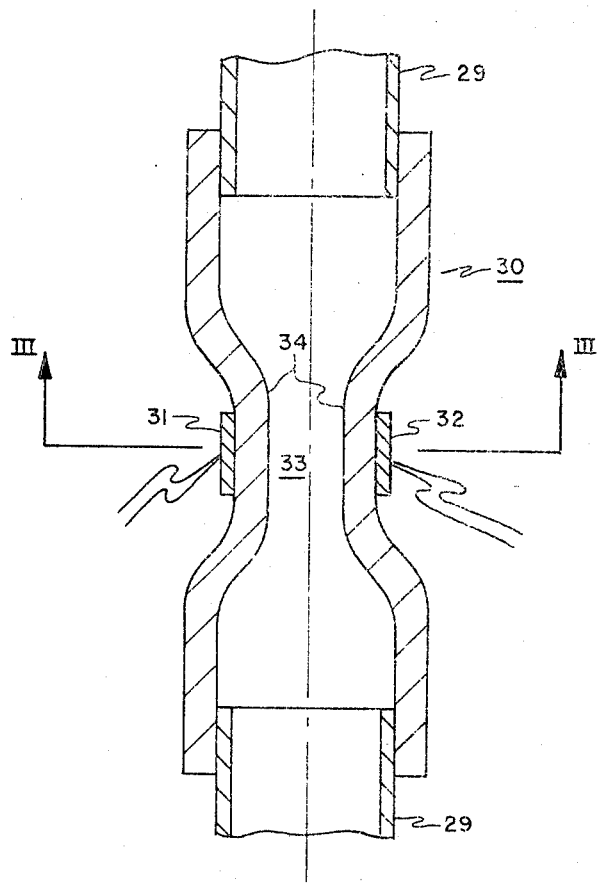
FIG. 2 is a longitudinal section view of the photodetecting window section of the continuous flow sample stream.
Figure 3:
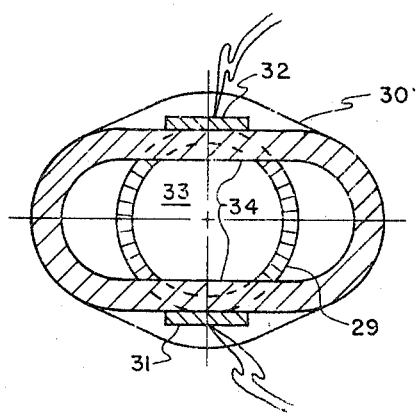
FIG. 3 is a cross-sectional view of the sample stream window taken along cut lines III—III of FIG. 2.

The window section 30 of the sample line 29 shown by FIGS. 2 and 3 may be simply devised from a short section of ½ inch i.d. thermoplastic tubing having a heat formed section 33 with generally parallel opposite side walls 34. To the outer surface of these parallel side walls 34 are bonded light source and detector elements 31 and 32. Prototype instruments used an Optron Inc., 1201 Tappan Circle, Carrollton, Texas 75006, OP214 LED light emitting diode for the light source 31 and a corresponding Optron Inc. OP603 light responsive diode for the detector 32.

Figure 4:
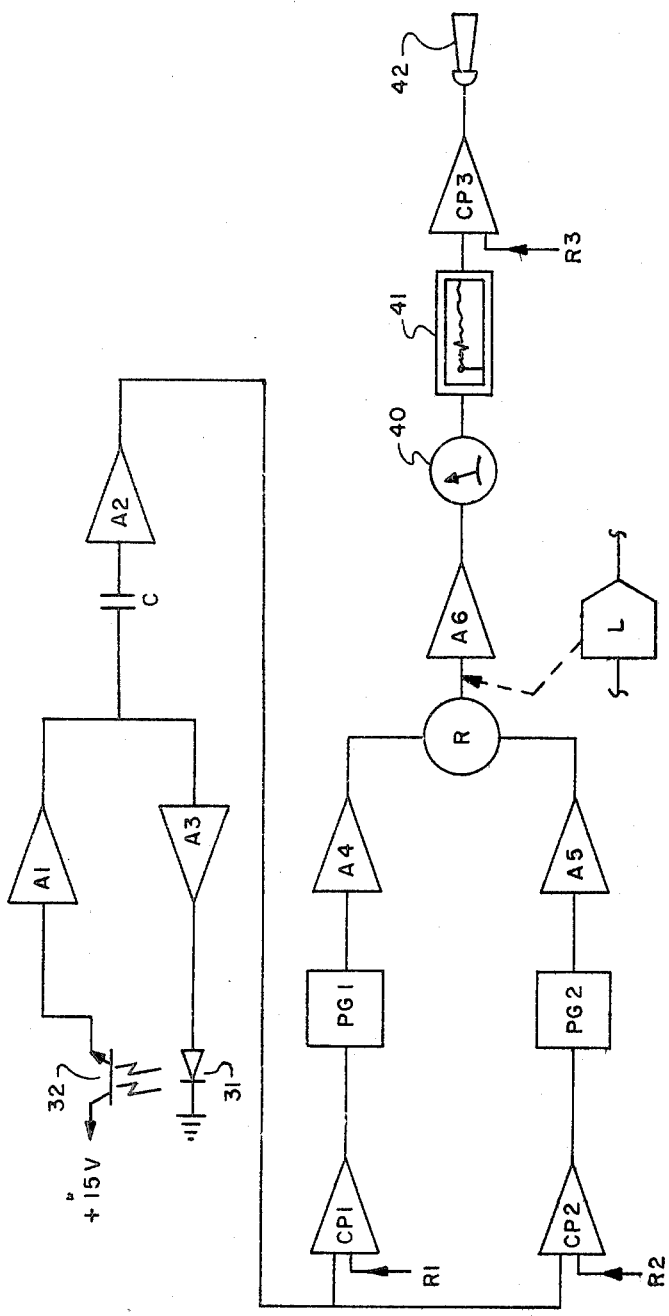
FIG. 4 is a signal flow schematic for the electronic portion of the meter.

Signal processing circuitry for the invention is schematically represented by FIG. 4 which shows the variable amplitude, direct current signal output of the sensor 32 first received by an amplifier A1 which increases the signal strength to a suitably higher value. National Semiconductors Ltd. of 331 Cornelia St., Plattsburgh, N.Y. manufactures an amplifier model LM 747 suitable for use in the A1 application.

The average d.c. value signal output of amplifier A1 is inverted and further amplified by an amplifier A3 such as the National Semiconductors model LM 751CV to power the light source 31 in such a way that a constant or steady-state average quantity of light is maintained on the sensor 32 notwithstanding water color, internal surface slimeing of the sample tube 29 or ageing of the light source 31.

Capacitance C filters the total signal from amplifier A1 to pass only pulse constituents due to shadows across the sensor 32 when particles in the slurry pass between the source 31 and sensor 32.

Amplifier A2 further magnifies the filtered pulse signal for amplitude discrimination by comparative amplifiers CP1 and CP2. These amplitude comparison devices are of a type such as the National Semiconductors model LM 319D which compare each incoming pulse from amplifier A2 with a predetermined reference value r1 and r2, respectively, and emit a corresponding pulse only if the incoming pulse equals or exceeds the reference value. In the present invention, the reference value of r1 is set four to five times greater than the value of r2 so that CP1 will transmit only those high amplitude pulses which signify the passage of a shive. Simultaneously, the value of r2 is set so that CP2 will transmit pulses representative of both fiber and shives.

Respective outputs from the comparative amplifiers CP1 and CP2 are conducted to pulse generators PG1 and PG2 such as the Signetics Corp., Wolf Rd. and Arques Ave., Sunnyvale, Calif., 555 timer which emits a constant amplitude, constant width, square wave pulse in response to each variable width, pulse received. These square wave pulses are repetitively averaged over brief intervals, 50 seconds for example, by amplifiers A4 and A5 such as the Analog Devices Inc., Rte. 1, Industrial Park, P.O. Box. 280, Norwood, Mass. 02062, AD 504 J which provides an analog responsive voltage variation proportional to the instant pulse receipt rate. At this juncture, the variable voltage signal of amplifiers A4 and A5 may be assigned a dimensional proportionality such as volts per shive per second in the case of A4 or volts per particle per second in the case of A5. These dimensions correspond to the fact that the momentary flow rate of both shives and total particles is being determined by an absolute event count over a brief time interval. The voltage of amplifiers A4 and A5 directly corresponds to the magnitude of the event count.

These voltage signals from the amplifiers A4 and A5 may be directly combined in a division function by ratio circuit R such an an Analog Devices, Inc., supra, AD530 which delivers a DC voltage signal proportional to the shive flow rate divided by the particle flow rate, a dimensionless value of the stated objective.

This dimensionless ratio signal may be further amplified by A6 to proportionately actuate an appropriately calibrated meter 40 or chart recorder 41.

Similarly, the ratio signal may be processed by a voltage comparison circuit CP3 similar to those of CP1 and CP2 which actuates an alarm 42 when the ratio signal value rises above an acceptable reference magnitude r3.

Figure 6:
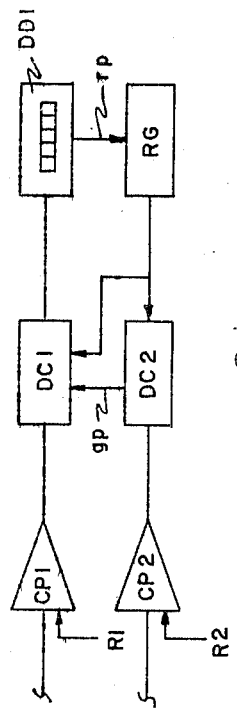
FIG. 6 schematically illustrates a digital signal embodiment of the system.

A digital signal management technique suitable for the present invention is represented by FIG. 6. As in the FIG. 4 analog system, comparative amplifiers CP1 and CP2 issue a pulse for each shive and particle, respectively. Responsive to a particle pulse train of n fiber pulses received by digital counter DC2, a gate pulse g.p. is issued to digital counter DC1 which is simultaneously counting the receipt of shive pulses. The beginning and end of gate pulse g.p. are used to start and stop the counting function of DC1.

At the end of each gate interval, the accumulated shive count in DC1, which represents the number of shives per n fiber particles, is transferred to a latch and display module DD1. Receipt of the shive count by DD1 initiates transmission of a reset signal to the counters DC1 and DC2 from a reset generator RG thereby resuming the particle and shive pulse counting interims.

This FIG. 6 digital embodiment of the invention provides the papermaker with a digital display of the objective dimensionless shive ratio.

Another signal management technique adaptable to the invention relates to a logarithmic scale of relative shive incidence. A logarithmic standard for acceptable pulp is subjective in that a plurality of pulp grade ranges are established above a worst-condition reference grade. Such a standard may begin with a sample of the highest shive incidence pulp a particular mill is known to produce. A standard handsheet is formed from this first sample and retained for future reference.

A portion of the first sample is diluted with shive-free pulp at some convenient ratio, 1:1 for example, to obtain a second sample from which a second, reference handsheet is formed and retained.

This process is repeated until a handsheet is formed which represents the lowest shive incidence pulp the mill is known to produce.

Although any dilution ratio may be used, the 1:1 ratio example represents a logarithmic system to the base 2 wherein each grade above the reference has half the absolute number of shives as the next grade lower. Distinctive about the log base 2 scale is that the human eye can consistently discern and accurately classify a handsheet from an unknown sample by mere visual comparison with the retained reference samples. Moreover, the degree of accuracy obtained is sufficient for most papermaking purposes.

Relating the present invention to such a shive incidence standard simply involves insertion of a log circuit L of the desired base in the signal flow stream following the ratio circuit R as represented by the dotted line arrow in FIG. 4. Such circuits are standard modular components of the type manufactured by Analog Devices Inc., supra, as catalog number AD755.

By converting the arithmetic ratio of shive incidence in a stock flow stream to the logarithm of that ratio, the total response scale of the instrument is greatly reduced and thereby more meaningful for production line consideration.

Figure 5:
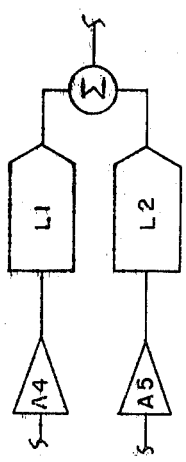
FIG. 5 schematically illustrates an alternative portion of the basic FIG. 4 signal management system.

Another obvious variation of this theme, shown by FIG. 5, is to convert the output signal of both A5 and A6 to proportional log functions by circuit modules L1 and L2 such as the Analog Devices AD756P similar to L above and merely subtract, by means of a simple summing circuit Σ, one signal from the other. The resulting difference is the same logarithm of the arithmetic ratio described above.

Figure 7:
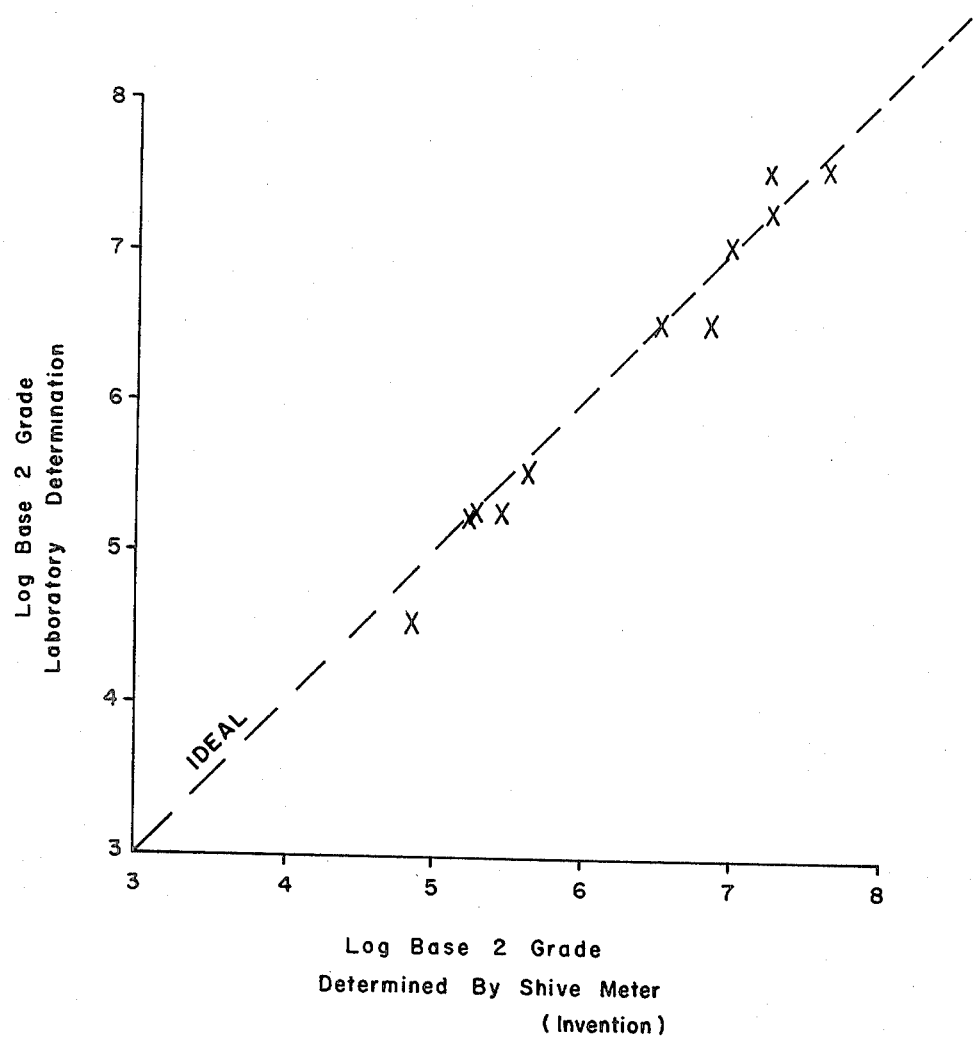
FIG. 7 is a comparative performance graph for the subject invention.

The graph of FIG. 7 represents typical performance of the invention as applied to a mill production stock stream. The graph ordinate scales laboratory determinations of shive incidence in a given pulp sample by skilled personnel. The graph abscissa scales the response of the subject invention to the same pulp sample. Comparison with the ideal correpondence rate illustrated by the dashed line testifies to the invention accuracy over a widely varying range of shive incidence.

In summary, therefore, the invention provides a direct, continuous sampling technique for extracting a representative fraction of a production flow stream for test purposes.

The shive meter, per se, detects and counts particles passing the window zone 33 by virtue of the shadow cast thereby on the photodetector cell 32. Simultaneously, shadows due to shives which are at least four times as great as shadows due to acceptable fiber bundles are discriminated exclusively on the basis of shadow size in a single light plane without regard to total volume.

Signal management techniques filter and screen the composite signal from the photodetector to separate base level d.c. values from the pulse values caused by passing particle shadows. Whether the particle source of the passing shadow was a shive or a fiber bundle is determined by the relative amplitude of the consequent pulse. Total particle pulses are inventoried along one signal line whereas shive particle caused pulses, simultaneously included with the total inventory are separately inventoried along another, parallel signal line.

The number of pulses in each signal line is countered over a fixed time interval identical to both lines. Thereby, corresponding pulse rates are provided. Division of one pulse rate by the other provides a dimensionless ratio between the two as a quantified indication of the relative shive incidence in the flow stream.

Note will be taken that this approach to the objective is independent of stock consistency beyond the point that two or more particles will cast a single shadow on the detector. This circumstance occurs with consistencies of greater than 0.1%. Therefore, so long as the sample consistency is less than 0.1%, consistency or flow rate variations are immaterial.

Having fully described our invention, we claim:

1. An apparatus for determining the relative presence of shives within a paper pulp slurry of 0.1% consistency or less comprising:
    a conduit having a transparent photodetector window for carrying a flow stream of said slurry therethrough;
    a photodetection cell comprising a light source and light sensor for generating a first electric signal responsive to the quantity of source light received by said sensor after passing through said window and a flow stream of said slurry therein;
    signal filter means for segregating variable amplitude pulse components of said first signal from an average d.c. value of said first signal and transmitting said variable amplitude pulse component as a second signal, said variable amplitude pulses being derived from the presence of particulates in said slurry flowing past said window and blocking the incidence of light on said sensor, the amplitude of each pulse being directly proportional to the size of the respective particle;
    comparative discriminator means responsive to said second signal to generate a third signal pulse for each pulse in said second signal having an amplitude exceeding a predetermined reference value distinctive to a shive particle;
    first pulse counting means for cyclically determining the number of second signal pulses received thereby in a fixed time interval and emitting a fourth signal that is cyclically adjusted and proportional to the time rate flow of said first signal pulses;
    second pulse counting means for cyclically determining the number of third signal pulses received therein in the same fixed time interval as applied to said first pulse counting means and emitting a cyclically adjusted fifth signal proportional to the time rate flow of said second signal pulses; and
    signal ratio means for combining said fourth and fifth signals to derive a relative proportionality therebetween and emit a sixth signal proportional to said relative proportionality.

2. An apparatus as described by claim 1 comprising means to emit a power signal to said light source that is inversely proportional to said average d.c. value.

3. Apparatus as described by claim 1 comprising first and second square wave generating means responsive to said second and third signal pulses, respectively, to emit a standardized pulse for each variable amplitude pulse received.

4. An apparatus as desrided by claim 1 wherein said signal ratio means comprises log means to determine a logarithmic function of said fourth and fifth signals and summing means to determine the arithmetic difference between said log functions.

5. An apparatus for determining the relative presence of shives in a production flow stream of paper pulp slurry, said apparatus comprising:
    A. sample extraction means for continuously extracting a sample flow of said paper pulp slurry from within a pressurized conduit carrying said production flow stream,
        said sample extraction means comprises means to form relatively high velocity jet of fiber-free water across a transversely disposed gap within said production flow stream into a receiving end of said sample conduit means to induct a fraction of said pulp slurry thereinto;

B. sample conduit means for delivering said sample flow through a photodetection window;

C. photodetection means comprising a light source and a light sensor operatively disposed on opposite sides of said window for generating a composite first signal having a variable amplitude pulsing constitutent responsive to the passage of fiber particles through said window, the amplitude of individual pulses being proportional to the size of respective, individual particles;

D. signal filter means for segregating said pulsing constitutent of said first signal form an average d.c. value thereof and transmitting said pulsing constituent as a second signal;

E. comparative discriminator means responsive to said second signal to generate a third signal pulse flow wherein each third signal pulse corresponds to a second signal pulse having an amplitude corresponding to a shive size particle in said sample flow;

F. first pulse counting means for cyclically determining the number of second signal pulses received thereby in a fixed time interval and emitting a cyclically adjusted first rate signal proportional to the time flow rate of said second signal pulses;

G. second pulse counting means for cyclically determining the number of said third signal pulses received thereby in said fixed time interval and emitting a cyclically adjusted second rate signal proportional to the time flow rate of said third signal pulses; and H. signal ratio means for combining said first and second rate signals to derive a relative proportionality therebetween and emit a signal proportional to said relative proportionality.

6. An apparatus as described by claim 5 comprising means to emit a power signal to said light source that is inversely proportional to said average d.c. value of said first signal for maintaining a relative constant strength level of said average d.c. value.

7. An apparatus as described by claim 5 comprising first and second square wave generating means responsive to said second and third signal pulses, respectively, to emit a standardized pulse for each variable amplitude pulse received thereby.

8. An apparatus as described by claim 5 wherein said signal ratio means comprises log means to determine a logarithmic function of said first and second rate signals and summing means to determine the arithmetic difference between said log functions.

9. An apparatus for determining the relative presence of shives within a paper pulp slurry of 0.1% consistency or less comprising:

A. A conduit having a transparent photodetector window for carrying a flow stream of said slurry therethrough;

B. A photodetection cell comprising a light source and light sensor for generating a first electric signal responsive to the quantity of source light received by said sensor after passing through said window and a flow stream of said slurry therein;

C. Signal filter means for segregating variable amplitude pulse components of said first signal from an average d.c. value of said first signal and transmitting said variable amplitude pulse component as a second signal, said variable amplitude pulses being derived from the presence of particulates in said slurry flowing past said window and blocking the incidence of light on said sensor, the amplitude of each pulse being directly proportional to the size of the respective particle;

D. Comparative discriminator means responsive to said second signal to generate a third signal pulse for each pulse in said second signal having an amplitude exceeding a predetermined reference value distinctive to a shive particle;

E. First pulse counting means for counting a predetermined number of second signal pulses received thereby and emitting a gate signal upon arrival at said predetermined number;

F. Second pulse counting means for counting the number of third signal pulses received thereby in a counting interim, said counted number of third signal pulses representing a ratio value of the number of shive partilces per predetermined number of slurry particles, said second pulse counting means including fourth signal means for emitting a fourth signal proportional to said ratio value; and G. Means responsive to said gate signal to terminate said counting interim and reset said first and second pulse counting means to a count reference point.

10. An apparatus as described by claim 9 wherein said gate signal responsive means comprises means responsive to said fourth signal from said second pulse counting means to digitally display the number of pulses received thereby during said counting interim.

* * * * *

UNITED STATES PATENT OFFICE
CERTIFICATE OF CORRECTION

PATENT NO. : 4,225,385
DATED : September 30, 1980
INVENTOR(S) : Horatio Hughes, Jr. & Robert A. Schilling It is certified that error appears in the above—identified patent and that said Letters Patent are hereby corrected as shown below:

Column 1, line 32, following "4-8" insert --mm--. Column 4, line 49, following "1/4" insert --inch--. Column 7, line 31, correct the spelling of "correspondence"; line 54, following "inventory" insert --,--. Column 8, line 37 (Claim 1, line 35), "therein" should be --thereby--.

Signed and Sealed this

Twenty-third Day of December 1980

[SEAL]

*Attest:*

SIDNEY A. DIAMOND

*Attesting Officer*   *Commissioner of Patents and Trademarks*